(12) United States Patent
Bae et al.

(10) Patent No.: US 7,396,127 B2
(45) Date of Patent: Jul. 8, 2008

(54) METHOD AND SYSTEM FOR QUANTIFYING DEGREE OF FATIGUE RESULTING FROM USE OF THREE-DIMENSIONAL DISPLAY

(75) Inventors: Soo-hyun Bae, Seoul (KR); Tae-hee Kim, Suwon-si (KR); Hee-seob Ryu, Suwon-si (KR); Jun-il Sohn, Yongin-si (KR); Min-kyu Park, Seongnam-si (KR); Yong-beom Lee, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 11/601,631

(22) Filed: Nov. 20, 2006

(65) Prior Publication Data

US 2007/0156348 A1 Jul. 5, 2007

(30) Foreign Application Priority Data

Dec. 30, 2005 (KR) .................. 10-2005-0135785

(51) Int. Cl.
*A61B 3/00* (2006.01)
*A61B 3/10* (2006.01)
*A61B 3/14* (2006.01)
(52) U.S. Cl. ................... 351/200; 351/205; 351/206
(58) Field of Classification Search ......... 351/200–223, 351/246
See application file for complete search history.

(56) References Cited

U.S. PATENT DOCUMENTS

2004/0070582 A1* 4/2004 Smith et al. ................. 345/419
2007/0019067 A1* 1/2007 Tsubaki et al. ............... 348/55

FOREIGN PATENT DOCUMENTS

| JP | 8-19520 | 1/1996 |
| JP | 9-23451 | 1/1997 |
| JP | 10-52402 | 2/1998 |
| KR | 10-0463345 | 12/2004 |

* cited by examiner

*Primary Examiner*—Mohammed Hasan
(74) *Attorney, Agent, or Firm*—Staas & Halsey LLP

(57) ABSTRACT

A method and system of quantitatively evaluating subjective inconvenience, e.g., physiological fatigue and emotional fatigue, experienced by a user when the user views a three-dimensional display screen, based on objectively measurable indices. The method includes sorting words representing a degree of fatigue associated with a 3D image display among a plurality of words, grouping the sorted words through factor analysis, setting words with the highest factor weight as subjective parameters, receiving evaluation scores for the subjective parameters while varying test values of objective parameter candidates capable of representing 3D image characteristics in numerical values, obtaining a correlation between each of indices for N groups and each of the objective parameter candidates using the evaluation scores, and applying the factor weight to the indices to represent the degree of fatigue in the objective parameter candidates.

17 Claims, 4 Drawing Sheets

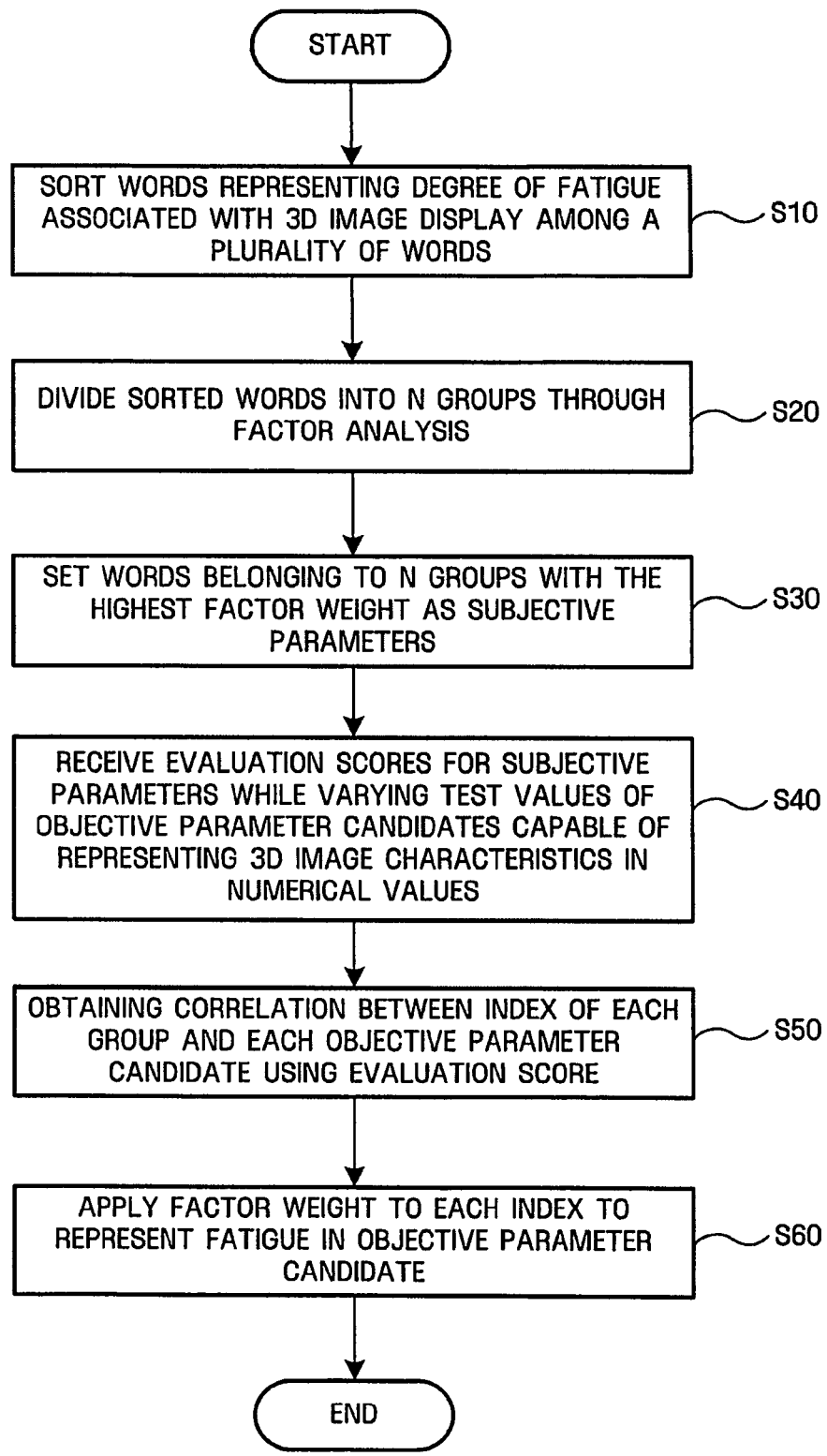

METHOD AND SYSTEM FOR QUANTIFYING DEGREE OF FATIGUE RESULTING FROM USE OF THREE-DIMENSIONAL DISPLAY

CROSS-REFERENCE TO RELATED APPLICATIONS

This application claims the benefit of Korean Patent Application No. 10-2005-0135785 filed on Dec. 30, 2005 in the Korean Intellectual Property Office, the disclosure of which is incorporated herein by reference in its entirety.

BACKGROUND OF THE INVENTION

1. Field of the Invention

The present invention relates to a method and system for quantitatively evaluating subjective inconvenience, e.g., physiological fatigue and emotional fatigue, experienced by a user when the user views a three-dimensional display screen, based on objectively measurable indices.

2. Description of the Related Art

When viewing a 3-dimensional (3D) image, a user of a 3D display system may experience inconvenience in vision, which may be crucially problematic in achieving commercialization of 3D display systems.

There are known systems for calculating a degree of ocular fatigue experienced by a 3D image display user.

When viewing a 3D image, users may experience physiological fatigue, e.g., dizziness or vomiting, as well as ocular fatigue. Thus, a variety of parameters, including the physiological fatigue, the ocular fatigue, and so on, must be taken into consideration to measure a degree of fatigue experienced by the user.

Among existing technologies for indirectly inferring a degree of 3D ocular fatigue using particular factors, Japanese Patent Laid-Open Publication No. 1997-023451 discloses a sensitivity response control apparatus detecting sensitivity information and controlling response outputs. In the disclosed patent, information about excited conditions is detected based on a temperature difference between the forehead and the nasal skin, and fatigue information is detected based on eye blinks. The intensity of a stereoscopic test pattern is adjusted based on the detection results.

Japanese Patent Laid-Open Application No. 1998-052402 discloses a visual fatigue estimation method based on presented test patterns, in which 3D image stimulations (stereoscopic eye chart) are presented with different period conditions to observe a user's visual evoked potential (VEP). In particular, according to the disclosed patent, if the user's VEP is periodically repeated, the left eye/right eye images blink. Conversely, if the user's VEP is not periodic, the left eye/right eye images are fused (combined) together. Based on the findings, the highest frequency of detecting blinks of the left eye/right eye images and the eye fatigue is inferred from the detected highest frequency (or shortest period).

Japanese Patent Laid-Open Application No. 1996-019520 discloses an eye fatigue determination technology in which movement of an eyeball is measured to generate digital data (entropy) corresponding to the eyeball movement and eye fatigue is determined if the entropy of eyeball movement representing eye fatigue increases over time.

Korean Patent Published Application No. 1999-016853 discloses a display parameter adjusting technology in which a user's papillary change is measured in a real-time basis for a predetermined period of time, a predetermined number of signals representing the user's papillary change measured for the predetermined period of time, the time-dependent papillary change applied through an image processor is analyzed based on predetermined program data, and pupil display parameters are adjusted according to a change in the area of the user's pupil.

As described above, a variety of techniques of understanding correlation between the user's particular response and eye fatigue and adjusting display parameters accordingly have been proposed. However, satisfactory techniques of quantifying the total degree of fatigue experienced by the user due to various causative parameters in the 3D image display system have not been developed.

Since the degree of fatigue applies to a 2D image display system as well as the 3D image display system, techniques for quantifying the user fatigue resulting from the use of the 3D or 2D image display system could be used as guidelines for development of the other of the 2D or 3D image display systems.

SUMMARY OF THE INVENTION

Accordingly, it is an aspect of the present invention to provide a method and system of filtering parameters of a degree of fatigue experienced by a user of a three-dimensional (3D) or two-dimensional (2D) image display system and quantifying the degree of fatigue resulting from the use of the 3D or 2D image display system.

Additional aspects and/or advantages of the invention will be set forth in part in the description which follows and, in part, will be apparent from the description, or may be learned by practice of the invention.

The foregoing and/or other aspects are achieved by providing a method of quantifying a degree of fatigue associated with a 3D image display, the method including sorting words representing a degree of fatigue associated with the 3D image display from among a plurality of words, dividing the sorted words into N groups through factor analysis, setting the divided words belonging to the N groups with a highest factor weight as subjective parameters, receiving evaluation scores for the subjective parameters while varying test values of objective parameter candidates representing 3D image characteristics in numerical values, obtaining a correlation between indices for each of the N groups and each of the objective parameter candidates using the evaluation scores, and applying the respective factor weights to the indices to represent the degree of fatigue in the objective parameter candidates.

The foregoing and/or other aspects are also achieved by providing a system quantifying a degree of fatigue associated with a 3D image display, the system including a word sorting unit sorting words representing a degree of fatigue associated with the 3D image display from among a plurality of words, a factor analyzing unit dividing the sorted words into N groups through factor analysis and setting the divided words belonging to the N groups with a highest factor weight as subjective parameters, a response input unit receiving evaluation scores for the subjective parameters while varying test values of objective parameter candidates representing 3D image characteristics in numerical values, and a correlation analyzing unit obtaining a correlation between each of indices for the N groups and the objective parameter candidates using the evaluation scores, and applying the respective factor weights to the indices to represent the degree of fatigue in the objective parameter candidates.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 4 is a flowchart illustrating a procedure executing a fatigue quantifying method according to the embodiment of the present invention of FIG. 1.

DETAILED DESCRIPTION OF THE PREFERRED EMBODIMENTS

Figure 1:
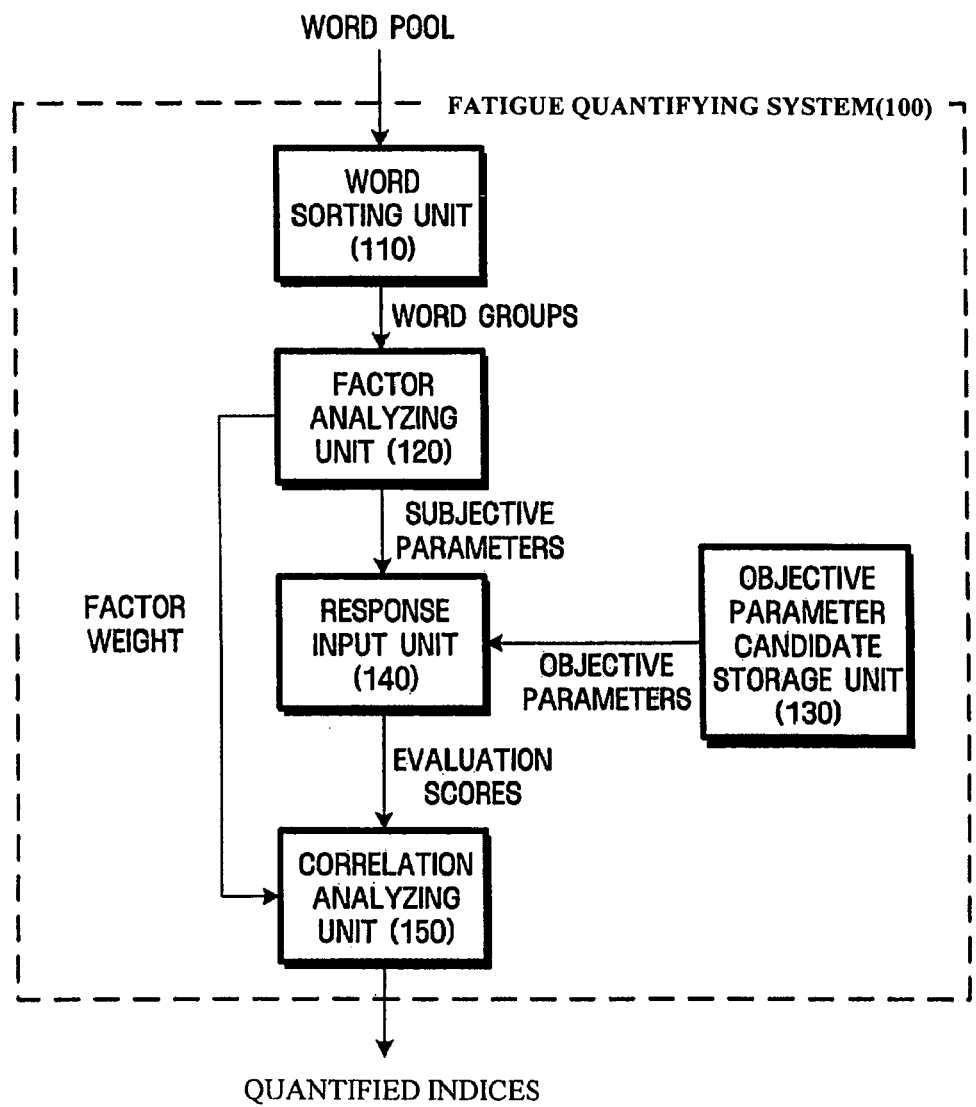
FIG. 1 is a block diagram of a fatigue quantifying system according to an embodiment of the present invention.

Reference will now be made in detail to the embodiments of the present invention, examples of which are illustrated in the accompanying drawings, wherein like reference numerals refer to the like elements throughout. The embodiments are described below to explain the present invention by referring to the figures.

In the embodiment of the present invention, a user response experiment was conducted to analyze a correlation between each of subjective fatigue evoking parameters and each of objective parameters through an operation of filtering physiological/emotional indices (subjective fatigue evoking parameters) of user's fatigue using 3D image simulations and an operation of adjusting measurable/adjustable parameters (subjective fatigue evoking objective parameters) in a 3D image display system.

A linear equation for fatigue estimation is constructed to quantitatively represent a degree of physiological fatigue and a degree of emotional fatigue based on values measured/analyzed in the filtering and adjusting operations, and parameters of the 3D image display system. The values are input through a parameter measuring device, and computed as fatigue indices using fatigue measurement software, thereby evaluating the fatigue indices of the 3D image display system.

FIG. 1 is a block diagram of a fatigue quantifying system 100 according to an embodiment of the present invention. The fatigue quantifying system 100 includes a word sorting unit 110, a factor analyzing unit 120, an objective parameter candidate storage unit 130, a response input unit 140, and a correlation analyzing unit 150. Although not shown in FIG. 1, the fatigue quantifying system 100 may further include a micro-processor controlling operations of various components shown in FIG. 1, and a random access memory (RAM) processing and loading the components in the form of a thread.

The word sorting unit 110 sorts out word groups each including a predetermined number of words from a word pool including a plurality of words related to a 3D image display.

For example, 2,721 adjectives are chosen at user's discretion and input to a word pool. Based on synonyms and use frequency, 260 words are selected in a primary sorting process. The primary sorting operation can be performed using known dictionary software. Among the primarily sorted 260 words, 182 words considered as being associated with 3D image display are filtered in a final sorting operation through a survey of 300 users.

For example, scores from 1 to 7 are assigned to each word. Seven is assigned to a word that is most closely related to a 3D image display and 1 is assigned to a word that is least closely related to the 3D image display. Finally, the 182 words are each assigned 300 scores (one per person), respectively, yielding 182×300 score data in total.

The finally filtered m words (i.e., m=182), that is, the sorted word groups and n score data (i.e., n=300) assigned to the words are supplied to the factor analyzing unit 120.

The factor analyzing unit 120 performs factor analysis on n score data for m words, that is, m×n score data in total, to determine the subjective parameters (the finally sorted words), and the factor weights of groups (or factors) to which the subjective parameters belong. The "factor analysis" may be performed using a variety of statistical software, such as SPSS (Statistical Package for the Social Science), SAS (Statistical Analysis System), MINITAB, or the like.

Figure 2:
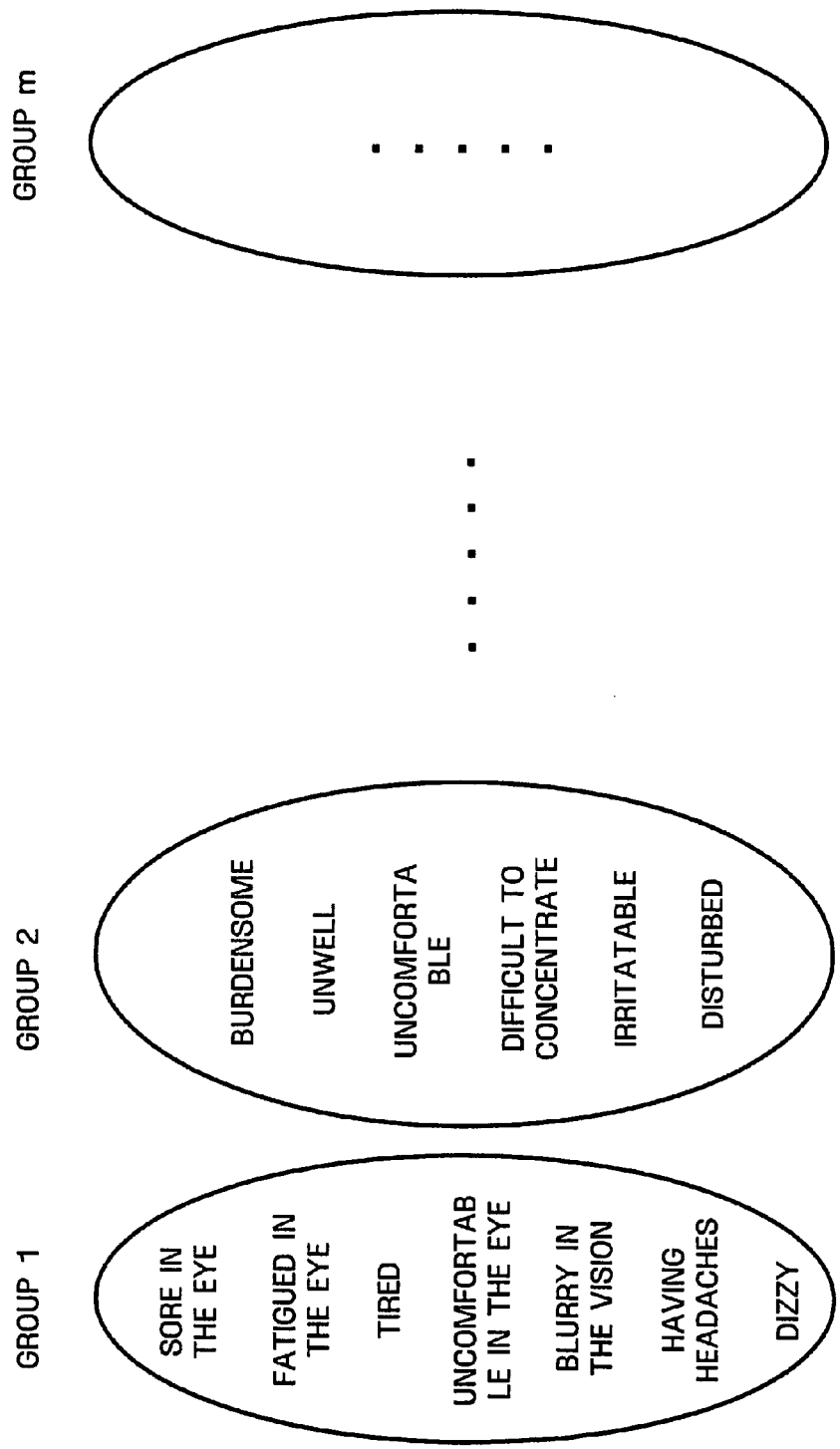
FIG. 2 illustrates an example of classifying words into a plurality of groups (factors) through factor analysis.

The results of the factor analysis demonstrate words belonging to m word groups or factors, and factor weights for the respective word groups, as shown in FIG. 2. Here, among the m word groups, a predetermined number of word groups having high factor weights are selected to determine the words belonging to the selected groups as subjective parameters.

For example, as shown in FIG. 2, assuming that the highest factor weight group is Group 1 and the second highest factor weight group is Group 2, 14 phrases included in Group 1 and Group 2 are chosen as subjective parameters. In consideration of common meanings of words for Group 1 and Group 2, Group 1 is referred to as a "physiological fatigue" group, and Group 2 is referred to as an "emotional fatigue" group.

The factor analysis demonstrates examples of physiological fatigue correlation and emotional fatigue correlation for the respective groups, as shown in Table 1.

TABLE 1

| Descriptive words | Physiological Fatigue Correlation | Emotional Fatigue Correlation |
| --- | --- | --- |
| Sore in the eye | .835 | |
| Fatigued in the eye | .823 | |
| Tired | .802 | |
| Strained in the eye | .739 | |
| Uncomfortable in the eye | .696 | |
| Dizzy | .656 | |
| Having headaches | .607 | |
| Blurry vision | .606 | |
| Burdensome | | .838 |
| Unwell | | .835 |
| Uncomfortable | | .749 |
| Difficult to concentrate | | .642 |
| Irritable | | .622 |
| Disturbed | | .617 |
| Eigen value (Factor weight) | 8.705 | 1.125 |
| Descriptor (%) | 50.100 | 11.673 |
| Cronbach | 0.895 | 0.826 |

Table 1 indicates that the correlations between the respective words and the groups are in a range of approximately 0.6 to approximately 0.85. The eigen value indicates a degree of relevancy, i.e., a factor weight, of each group with the 3D image display system. The eigen value is similar to a descriptor, which serves to describe or identify a percentile (%) of the 3D image display system by each group.

In Table 1, a Cronbach's value is an index representing the internal consistency of parameters (words) and a level of greater than 0.8 is typically desirable. If a difference between correlations of two similar words is very large, the Cronbach's value would not be reliable. For example, a correlation of a word "dizzy" (0.607) and a correlation (0.606) of a word "having headaches" is quite small.

The factor analyzing unit 120 selects the 14 words as the subjective parameters because these words are all highly correlated with one another and have a highly reliable Cronbach's value by group. If the correlation or Cronbach's value is not reliable, the word sorting unit 110 performs a word group sorting procedure again.

Eventually, the factor analyzing unit 120 may obtain the subjective parameters and factor weights of groups to which the subjective parameters belong through factor analysis. The subjective parameters are supplied to the response input unit 140 and the factor weights are supplied to the correlation analyzing unit 150, respectively.

Referring back to FIG. 1, the response input unit 140 receives the subjective parameters, and objective parameter candidates from the objective parameter candidate storage unit 130.

Here, the objective parameter candidates are experimental parameters estimated to be associated with the fatigue in a 3D image display. The objective parameter candidates include at least one selected among crosstalk, FOV (Field of View), focus distance, distance, scale, rotation, biocular brightness, monocular brightness, biocular contrast, monocular contrast, biocular sharpness, and monocular sharpness.

The response input unit 140 displays test 3D screens for examinees while varying objective parameter candidates, and allows the examinees to input scores for the subjective parameters (e.g., one grade among 1-7). The higher the score, the more intense the sensation represented by a particular subjective parameter (word). This examination procedure is repetitively performed on a sufficient number of examinees.

Figure 3:
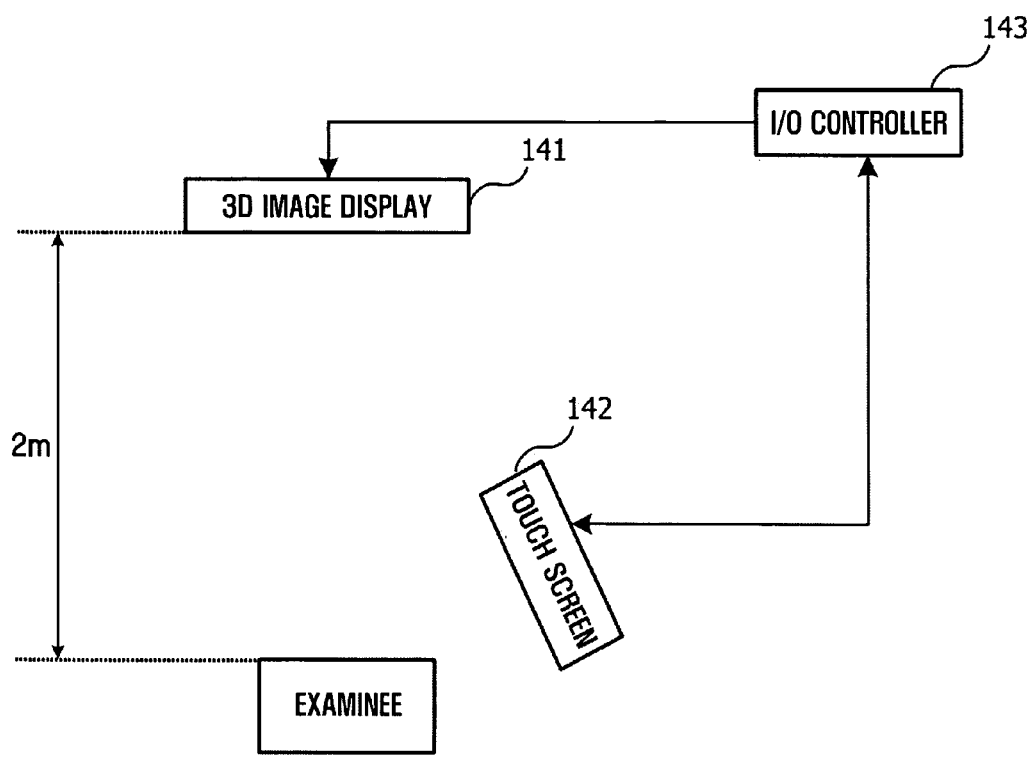
FIG. 3 is a detailed block diagram of a response input unit in the fatigue quantifying system shown in FIG. 1.

As shown in FIG. 3, the response input unit 140 comprises a 3D image display 141, a touch screen 142, and an input/output controller 143.

The 3D image display 141 displays the test 3D screen to the examinees depending on the change of the objective parameters under the control of the input/output controller 143. The 3D image display 141 may be an LCD (Liquid Crystal Display), an LED (Light-Emitting Diode), an OLED (Organic Light-Emitting Diode), a PDP (Plasma Display Panel), or other image display.

The touch screen 142 presents subjective parameters to the examinees under the control of the input/output controller 143, and allows the examinees to input a score for a particular subjective parameter.

The input/output controller 143 controls the 3D image display 141 to output the test 3D screen to the examinees while varying objective parameter candidates supplied from the objective parameter candidate storage unit 130, and controls the touch screen 142 to present the subjective parameters to the examinees and the scores for the subjective parameters input from the touch screen 142 to be supplied to the correlation analyzing unit 150.

Suppose there are 19 objective parameter candidates in total. Then, 4 to 6 test values for each objective parameter candidate are chosen. For example, test values 20%, 40%, 60%, and 80% are assigned to the objective parameter candidate "brightness". Then, 3D images for the respective test values of the objective parameter candidate are displayed to the examinees. For example, if 5 test values are used, 95 possible images are displayed to the examinees. Of course, this procedure is repetitively performed on a sufficient number of examinees.

Thus, the response input unit 140 supplies the correlation analyzing unit 150 with evaluation scores equal to "Number of test values×Number of examinees×Number of subjective parameters".

The correlation analyzing unit 150 obtains the correlation between each of the subjective parameters and each of the objective parameter candidates using the evaluation scores. Here, the objective parameter candidates include the remaining objective parameter candidates with the exception of objective parameter candidates considered as being less correlated with the subjective parameters.

One representative method of obtaining the correlation is multiple regression analysis. The multiple regression analysis may be implemented by SPSS, SAS, MINITAB or other various statistical software techniques. The multiple regression analysis is generally performed to determine how two or more independent factors (effect parameters, cause parameters, etc.) affect dependent factors (result parameters). Therefore, effects of independent factors relative to dependent factors can be determined by the multiple regression analysis, and changes in the dependent factors with changes of independent factors can be statistically estimated.

In the multiple regression analysis, the independent factors are objective parameter candidates, and the dependent factors are physiological fatigue indices (Group 1) and emotional fatigue indices (Group 2).

When the physiological fatigue index or emotional fatigue index is denoted by Y and the objective parameter candidates are denoted by $x_1$ through $x_k$, where k is the number of objective parameter candidates, the linear regression equation is established as Equation 1:

$$Y = \beta_0 + \beta_1 x_1 + \beta_2 x_2 + \ldots + \beta_k x_k + \epsilon \qquad \text{Equation 1}$$

where $\beta_k$ is a weight coefficient for each objective parameter, and $\epsilon$ is an error.

Table 2 demonstrates the results of the multiple regression analysis for physiological fatigue. Among 19 objective parameter candidates, 7 objective parameters were chosen.

TABLE 2

| Physiological fatigue | β | SEB | β* | P |
|---|---|---|---|---|
| (Constant) | 4.511 | 1.043 | | 0.000 |
| Rotation | 2.923 | 0.257 | 0.238 | 0.000 |
| Monocular Brightness | 4.998 | 0.621 | 0.169 | 0.000 |
| Monocular Sharpness | 0.144 | 0.026 | 0.114 | 0.000 |
| Biocular Brightness | 2.945 | 0.614 | 0.100 | 0.000 |
| Scale | −1.434 | 0.450 | −0.067 | 0.001 |
| Biocular Contrast | 1.664 | 0.620 | 0.056 | 0.007 |
| Distance | 1.843 | 0.840 | 0.046 | 0.028 |

In Table 2, β represents a weight coefficient, SEB represents a standard error of the weight coefficient, β* represents a normalized weight coefficient, and P represents a significance probability.

If a level of a significance probability P is lower than a significance level, it suggests that the objective parameter is reliable. If the significance level is set to 0.03 (3%) or less, it is determined that the objective parameters shown in Table 2 are all reliable. In general, no matter how large the β level is, if the significance probability exceeds the significance level, the objective parameter is discarded.

If a level of a significance probability P is lower than a significance level, it suggests that the objective parameter is reliable. If the significance level is set to 0.03 (3%) or less, it is determined that the objective parameters shown in Table 2 are all reliable. In general, no matter how large the β level is, if the significance probability exceeds the significance level, the objective parameter is discarded.

Using Equation 1 and Table 2, the physiological fatigue index ($Y_1$) is computed as:

$Y_1$=4.511+2.923×Rotation+4.998×Monocular Brightness+0.144×Monocular Sharpness+2.945×Biocular Brightness+1.664×Biocular Contrast+1.843×Distance−1.434×Scale          Equation 2

Table 3 demonstrates the results of the multiple regression analysis for emotional fatigue. Here, 9 objective parameters were chosen among 19 objective parameter candidates. A summary of the objective parameters shown in Table 2 and the objective parameters shown in Table 3 demonstrates the effects of a total of 11 objective parameters on physiological fatigue and/or emotional fatigue.

TABLE 3

| Emotional fatigue | B | SEB | β | P |
| --- | --- | --- | --- | --- |
| (Constant) | 6.356 | 1.553 |  | 0.000 |
| Rotate | 3.238 | 0.250 | 0.270 | 0.000 |
| Monocular Sharpness | 0.171 | 0.026 | 0.138 | 0.000 |
| Monocular Brightness | 3.908 | 0.603 | 0.134 | 0.000 |
| Biocular Brightness | 3.119 | 0.594 | 0.108 | 0.000 |
| Biocular Sharpness | 0.077 | 0.027 | 0.059 | 0.005 |
| Monocular Contrast | 1.412 | 0.588 | 0.050 | 0.016 |
| FOV | −0.067 | 0.026 | −0.054 | 0.009 |
| Focus Distance | −0.175 | 0.069 | −0.053 | 0.011 |
| Scale | −0.910 | 0.435 | −0.043 | 0.037 |

Based on Equation 1 and Table 3, the emotional fatigue index ($Y_2$) can be calculated using Equation 3:

$Y_2$=6.356+3.238×Rotation+0.171×Monocular Sharpness+3.908×Monocular Brightness+3.119×Biocular Brightness+1.412×Monocular Contrast+0.077×Biocular Sharpness−0.067×$FOV$−0.175×Focus Distance−0.910×Scale          Equation 3

The correlation analyzing unit 150 applies the factor weights supplied from the factor analyzing unit 120 to the respective groups (for physiological fatigue and emotional fatigue) to obtain the total fatigue index ($Y_0$). The total fatigue index ($Y_0$) can be obtained using Equation 4:

$Y_0 = a_1 \times Y_1 + a_2 \times Y_2$          Equation 4 wherein $a_1$ and $a_2$ are factor weights for the respective groups, e.g., 8.705 and 1.125, based on the results shown in Table 1. In this case, the total fatigue index ($Y_0$) is eventually written as:

$Y_0$=46.42+47.91×Monocular Brightness+29.15×Biocular Brightness+29.08×Rotation+16.04×Distance+14.49×Biocular Contrast+1.59×Monocular Contrast+1.44×Monocular Sharpness+0.09×Biocular Sharpness−13.5×Scale−0.2×Focus Distance−0.08×$FOV$          Equation 5

The respective components shown in FIG. 1 may be implemented by software components executed in a predetermined area of a memory, such as task, class, subroutine, process, object, execution thread, or program components, or hardware components, such as FPGA (field-programmable gate array) or ASIC (application-specific integrated circuit). The functionality provided by the components and modules may be combined into fewer components and modules or further separated into additional components and modules. In addition, the components and modules may be implemented such that they execute one or more computers in a communication system.

FIG. 4 is a flowchart illustrating a procedure for executing a fatigue qualifying method according to the embodiment of the present invention.

In operation S10, words representing fatigue associated with the 3D image display are sorted among a plurality of words. Operation S10 is divided into sub-steps: filtering adjectives among the plurality of words; grouping the filtered adjectives into several groups on the basis of synonyms and use frequency; and further sorting words associated with the 3D image display among the sorted adjectives.

The factor analyzing unit 120 analyzes the sorted words to divide the same into N groups through factor analysis in operation S20 (N is a natural number). Among the groups, the words belonging to N groups having the highest factor weight are set as subjective parameters in operation S30. Here, the N groups may include a physiological fatigue group, and an emotional fatigue group.

The factor analyzing unit 120 obtains a Cronbach's value for each of the N groups and selects only the groups having the Cronbach's value exceeding a predetermined threshold. If an appropriate group is not selected, the operation S10 may be repeatedly performed.

The response input unit 140 receives evaluation scores for the subjective parameters while varying test values of objective parameter candidates capable of representing the 3D image characteristics in numerical values in operation S40.

The operation S40 can be divided into substeps: displaying images obtained by varying the test values of the objective parameter candidates and the subjective parameters to a plurality of examinees; and allowing the plurality of examinees to input evaluation scores for the subjective parameters.

The correlation analyzing unit 150 obtains a correlation between an index of each of the N groups and each of the objective parameter candidates using the input evaluation score values in operation S50. In an exemplary embodiment, the correlation analyzing unit 150 executes operation S50 by performing multiple regression analysis with indices for the N groups as dependent factors and the objective parameter candidates as independent factors.

The correlation analyzing unit 150 represents the indices or the degree of fatigue as the objective parameters having a significance probability of not greater than a predetermined level among the objective parameter candidates.

Then, a factor weight is applied to each of the respective indices to represent the degree of fatigue in the objective parameter candidates in operation S60. The objective parameter candidates include at least one selected among crosstalk, FOV (Field of View), focus distance, distance, scale, rotation, biocular brightness, monocular brightness, biocular contrast, monocular contrast, biocular sharpness, and monocular sharpness.

As described above, according to the present application, since the quantifying system of the user's fatigue, which is the crucial problem in realizing commercialization of 3D image display systems, is attained, it is possible to propose guidelines for development of 3D image display systems.

Although an embodiment of the present invention has been shown and described, it would be appreciated by those skilled in the art that changes may be made in this embodiment without departing from the principles and spirit of the invention, the scope of which is defined in the claims and their equivalents.

What is claimed is:

1. A method of quantifying a degree of fatigue to a user viewing a 3D image display, the method comprising:
   sorting words representing a degree of fatigue associated with the 3D image display from among a plurality of words;
   dividing the sorted words into a plurality of groups through factor analysis;

setting the divided words belonging to the plurality of groups with a highest factor weight as subjective parameters;

receiving evaluation scores for the subjective parameters while varying test values of objective parameter candidates representing 3D image characteristics in numerical values;

obtaining a correlation between indices for each of the plurality of groups and each of the objective parameter candidates using the evaluation scores; and applying the respective factor weights to the indices to represent the degree of fatigue in the objective parameter candidates.

2. The method of claim 1, wherein the sorting of the words comprises:

filtering adjectives from among the plurality of words;

grouping the filtered adjectives based on synonyms and use frequency; and sorting adjectives associated with the 3D image display from among the filtered adjectives.

3. The method of claim 1, wherein the plurality of groups include a physiological fatigue group and an emotional fatigue group.

4. The method of claim 1, further comprising verifying by Cronbach's values for the plurality of groups, comprising setting a reliability of the words set as subjective parameters.

5. The method of claim 1, wherein the receiving of the evaluation scores comprises:

displaying images obtained by the varying of the test values of the objective parameter candidates to a plurality of examinees;

displaying the subjective parameters to a plurality of examinees; and inputting evaluation scores for the subjective parameters by the plurality of examinees.

6. The method of claim 1, wherein the obtaining of the correlation comprises using a multiple regression analysis in which the indices for the plurality of groups are used as dependent factors and the objective parameter candidates are used as independent factors.

7. The method of claim 1, wherein the varied objective parameter candidates and the applying of the factor weight to the indices exceeds a predetermined significance probability.

8. The method of claim 1, wherein the objective parameter candidates include crosstalk, field of view, focus distance, distance, scale, rotation, biocular brightness, monocular brightness, biocular contrast, monocular contrast, biocular sharpness, or monocular sharpness.

9. The method of claim 1, wherein the dividing into plurality of groups comprises dividing into a natural number of the groups.

10. A system quantifying a degree of fatigue to a user viewing a 3D image display, the system comprising:

a word sorting unit sorting words representing a degree of fatigue associated with the 3D image display from among a plurality of words;

a factor analyzing unit dividing the sorted words into a plurality of groups through factor analysis and setting the divided words belonging to the plurality of groups with a highest factor weight as subjective parameters;

a response input unit receiving evaluation scores for the subjective parameters while varying test values of objective parameter candidates representing 3D image characteristics in numerical values; and a correlation analyzing unit obtaining a correlation between indices for the plurality of groups and each of the objective parameter candidates using the evaluation scores, and applying the respective factor weights to the indices to represent the degree of fatigue in the objective parameter candidates.

11. The system of claim 10, wherein the word sorting unit filters adjectives from among the plurality of words, sorts the filtered adjectives based on synonyms and use frequency, and sorts adjectives associated with the 3D image display from among the filtered adjectives.

12. The system of claim 10, wherein the plurality of groups include a physiological fatigue group and an emotional fatigue group.

13. The system of claim 10, wherein the factor analyzing unit obtains Cronbach's values for the plurality of groups, and the Cronbach's values exceed a predetermined significance probability.

14. The system of claim 10, wherein the response input unit displays images obtained by the varying of the test values of the objective parameter candidates, and the subjective parameters to a plurality of examinees, and the plurality of examinees displays input evaluation scores for the subjective parameters to the response input unit.

15. The system of claim 10, wherein the correlation analyzing unit performs a multiple regression analysis in which the indices for the plurality of groups are used as dependent factors and the objective parameter candidates are used as independent factors.

16. The system of claim 10, wherein the correlation analyzing unit represents the indices or the degree of fatigue by objective parameters exceeding a predetermined significance probability from among the objective parameter candidates.

17. The system of claim 10, wherein the objective parameter candidates include crosstalk, field of view, focus distance, distance, scale, rotation, biocular brightness, monocular brightness, biocular contrast, monocular contrast, biocular sharpness, or monocular sharpness.

* * * * *